United States Patent [19]

Falconer et al.

[11] 4,431,852
[45] Feb. 14, 1984

[54] HALOHYDRINS

[75] Inventors: James A. Falconer, Falkirk; Raymond V. H. Jones, Linlithgow; Ian G. C. Fleming, Kirkliston, all of Scotland

[73] Assignee: Imperial Chemical Industries Limited, London, England

[21] Appl. No.: 370,815

[22] Filed: Apr. 22, 1982

[30] Foreign Application Priority Data

May 12, 1981 [GB] United Kingdom ............... 8114396

[51] Int. Cl.$^3$ ............................................. C07C 33/34
[52] U.S. Cl. .................................. 568/809; 568/841; 568/842; 568/844
[58] Field of Search ............... 568/809, 812, 841, 844, 568/842

[56] References Cited

U.S. PATENT DOCUMENTS

| | | | |
|---|---|---|---|
| 3,100,232 | 8/1963 | Keith et al. | 568/812 |
| 3,465,046 | 9/1969 | Borchert et al. | 568/812 |
| 3,786,084 | 1/1974 | D'Ostrowick | 568/812 |
| 3,793,380 | 2/1974 | D'Ostrowick | 568/812 |
| 3,819,722 | 6/1974 | Bertin et al. | 568/812 |
| 3,845,145 | 10/1974 | Wojtowicz et al. | 568/812 |

FOREIGN PATENT DOCUMENTS

| | | | |
|---|---|---|---|
| 17080 | 3/1980 | European Pat. Off. | 568/809 |
| 15756 | 9/1980 | European Pat. Off. | 568/809 |
| 1172654 | 6/1964 | Fed. Rep. of Germany | 568/809 |
| 1132034 | 8/1968 | United Kingdom | 568/809 |
| 1144063 | 3/1969 | United Kingdom | 568/809 |

OTHER PUBLICATIONS

Sumerall et al. "Canadian J. of Chem." vol. 42p (1964) pp. 2896–2899.
Guss et al. "J. Amer. Chem. Soc." vol. 77 (1955) p. 2549.
Grummitt et al. "J. Amer. Chem. Soc." vol. 72 (1950) pp. 2279–2280.
Reid et al. "J. Chemical Society" (1982) pp. 1487–1493.

Primary Examiner—Werren B. Lone
Attorney, Agent, or Firm—Cushman, Darby & Cushman

[57] ABSTRACT

Compounds of the formula:

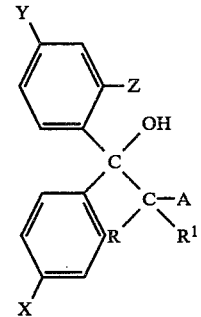

wherein R and $R^1$, which may be the same or different, are hydrogen or alkyl; X, Y and Z are each independently hydrogen, chlorine or fluorine and A is chlorine or bromine, are prepared by reacting a tertiary alcohol of general formula:

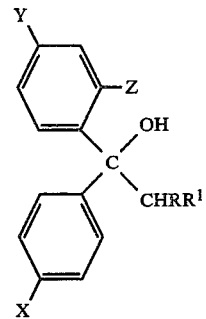

or a substituted alkene of general formula:

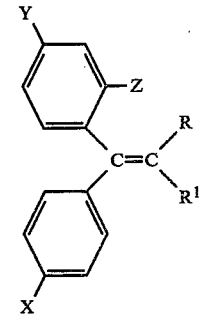

with chlorine, bromine, hypochlorous acid or hypobromous acid in water at a pH not exceeding 7 and at a temperature from 10° to 150° C.

The compounds are useful intermediates for fungicides.

2 Claims, No Drawings

HALOHYDRINS

This invention relates to a process for the preparation of halohydrins, more specifically 1,1-bis [(optionally substituted)phenyl]-2-haloalkan-1-ols, and to certain novel compounds obtained therefrom.

According to the present invention there is provided a process for the preparation of halohydrins of formula (I):

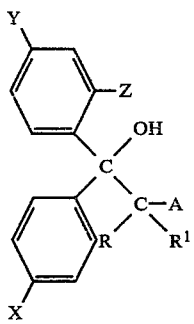

wherein R and R$^1$, which may be the same or different, are hydrogen or alkyl, preferably C$_1$–C$_4$ alkyl; X, Y and Z are each independently hydrogen, chlorine or fluorine and A is chlorine or bromine, which comprises reacting a tertiary alcohol of general formula (II):

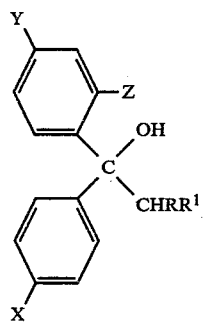

or a substituted alkene of general formula (III):

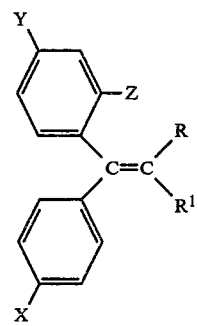

wherein R, R$^1$, X, Y and Z have the previously defined meanings, with chlorine, bromine, hypochlorous acid or hypobromous acid in water at a pH not exceeding 7 and at a temperature from 10° to 150° C.

This process may be carried out either batchwise or continuously.

If hypochlorous acid or hypobromous acid are used in the process they may be added in the form of a dilute aqueous solution or they may, if desired, be generated in situ by addition of an aqueous solution of a salt such as an alkali metal salt, e.g. the sodium or potassium salt, or an alkaline earth metal salt, e.g. the calcium salt, of hypochlorous acid or hypobromous acid, to the reaction mixture. A particularly preferred salt of hypochlorous acid is sodium hypochlorite because of its commercial availability in the form of an aqueous solution.

Alternatively a mixture of a halide salt and an oxyhalide salt, for example, a mixture of a bromide and a bromate, may be used.

The process is conveniently carried out at the reflux temperature (ca.100° C.) of the aqueous reaction medium by slowly adding the chlorine, bromine, dilute aqueous solution of hypochlorous acid or hypobromous acid, or an aqueous solution of a salt of hypochlorous acid or hypobromous acid as indicated above, to a vigorously agitated mixture of water and the tertiary alcohol of formula (II) or the substituted alkene of formula (III), previously adjusted to a low pH by addition of an acid such as hydrochloric acid. A pH of about 1.0 is suitable. The product may then be isolated from the aqueous reaction mixture in known manner, for example, by extraction with a water-immiscible solvent and subsequent removal of the solvent from the extract by evaporation or distillation.

The starting materials of formula (II) which may be used in the process of the invention may be obtained by a Grignard reaction between an alkyl magnesium halide of formula (IV):

$$RR^1HCMg.Hal \qquad (IV)$$

and a benzophenone of formula (V):

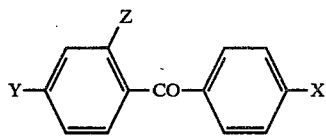

wherein R, R$^1$, X, Y and Z have the previously defined meanings and Hal is chlorine, bromine or iodine, under conditions known from the literature for the conduct of such reactions.

The benzophenones of formula (V) may be prepared in known manner by Friedel-Crafts reaction between a benzoyl halide of formula (VI):

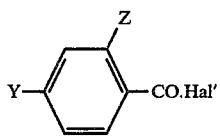

and a benzene derivative of formula (VII):

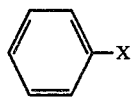

wherein X, Y and Z have the previously defined meanings and Hal' represents bromine or preferably chlorine, in the presence of a Lewis acid such as aluminium chloride.

Alternatively, the starting materials of formula (II) may be obtained by reaction in known manner of a compound of formula (VIII):

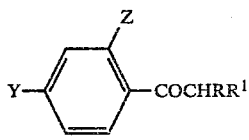

(VIII)

wherein R, R¹, Y and Z have the previously defined meanings, with a Grignard compound of formula (IX):

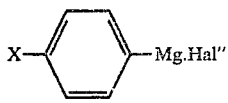

(IX)

wherein Hal" is bromine or iodine. The compounds of formula (VIII) may be obtained by methods known from the art, for example, by Friedel-Crafts reaction of an acid halide of formula (X):

RR¹CH.COA     (X)

wherein A, R and R¹ have the previously defined meanings, with a benzene derivative of formula (XI):

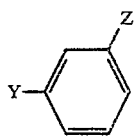

(XI)

In a still further alternative, the tertiary alcohols of formula (II) in which X and Y are the same and Z is hydrogen may be prepared by reaction in known manner between 2 mol proportions of a Grignard compound of formula (IX) and 1 mol proportion of an ester of formula (XII):

RR¹CH.COOR²     (XII)

wherein R, R¹ and R² have the previously defined meanings. An example of an ester of formula (XII) which may be used in the process is ethyl acetate.

The substituted alkenes of formula (III) which may also be used as starting materials in the preparation of the halohydrins of formula (I) may be obtained by dehydration of a tertiary alcohol of formula (II) using methods known from the literature for such dehydrations, for example, by heating the alcohol of formula (II) in the presence of a catalytic amount of a strong acid such as p-toluenesulphonic acid.

The substituted alkenes of formula (III) may also be obtained directly from the Grignard reaction between an alkyl magnesium halide of formula (IV) and a benzophenone of formula (V) as already indicated above, without isolation of the intermediate alcohol of formula (II). The Grignard reaction mixture, after completion of the reaction, is poured into dilute aqueous acid, and the organic layer collected. This organic layer contains the alcohol of formula (II) in the organic solvent or mixture of organic solvents, for example, a mixture of tetrahydrofuran and toluene, which was used in carrying out the preparation of Grignard compound and its subsequent reaction with the benzophenone. A dehydrating agent is added to the organic layer and the whole heated to effect dehydration of the intermediate alcohol.

The halohydrins of formula (I) are useful intermediates for fungicides. Those in which R and R¹ are both hydrogen are intermediates for the preparation of fungicidal compounds of formula (XIII):

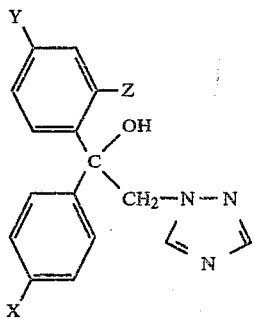

(XIII)

wherein X, Y and Z have the previously defined meanings.

Compounds of formula (XIII) and methods for their preparation including that from a halohydrin of formula (I), are disclosed in European Patent Application No. 0015756.

Normally they will be obtained via the epoxide of formula (XIV):

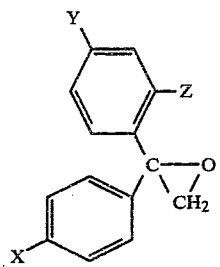

(XIV)

which is readily formed from the halohydrin under the normally basic conditions of the triazole addition.

Particularly useful halohydrins of formula (I) for the synthesis of fungicidal compounds of formula (XIII) are those in which R and R¹ are hydrogen and at least one of X, Y and Z is chlorine or fluorine and especially in which R and R¹ are hydrogen and X, Y and Z have the following substitution patterns:

| X  | Y  | Z  |
|----|----|----|
| F  | F  | H  |
| F  | H  | F  |
| F  | H  | Cl |
| Cl | H  | Cl |
| Cl | F  | H  |
| F  | Cl | Cl |

These halohydrins form another aspect of the present invention.

The invention is illustrated by the following Examples in which parts and percentages are by weight.

EXAMPLE 1

To a vigorously stirred mixture of 1,1-bis(4-fluorophenyl)ethanol (6 parts) in water (300 parts) at reflux (ca. 100° C.) and pH 1.0 is added a diluted aqueous solution of commercial sodium hypochlorite (75 parts; ca 4% w/v available chlorine) over 2.5 hours. The pH after this addition is ca. 1.0. After cooling the product separates as an oil which is extracted with carbon tetrachloride. After removal of the solvent from the organic layer, the actual weight yield of 1,1-bis(4-fluorophenyl)-2-chloroethanol is 10.6 parts (strength 29.4%, determined by p.m.r. spectroscopy) which represents 47.4% of theory.

The 1,1-bis(4-fluorophenyl)ethanol used in this Example is prepared as follows:

A solution of methyl bromide (89 parts) in toluene (52 parts) is added, over about 30 minutes, to a stirred mixture of magnesium turnings (20 parts), toluene (156 parts) and tetrahydrofuran (122 parts), maintaining the temperature at 30°–40° C. After the magnesium is dissolved 4,4'-difluorobenzophenone (168 parts) is added, whilst maintaining the temperature at 25°–30° C. The mixture is drowned out into 5% aqueous ammonium chloride (1500 parts) and stirred for 30 minutes. The organic layer is separated, dried over anhydrous sodium sulphate and the solvent removed, under vacuum, at less than 40° C., to leave a brown oil (170 parts) containing 90% (by GLC, 10% SE30 at 200° C.) of 1,1-bis(4-fluorophenyl)ethanol (85% conversion based on 4,4'-difluorobenzophenone). Distillation under vacuum, from sodium carbonate, gives 1,1-bis(4-fluorophenyl)ethanol contaminated with a small amount of 1,1-bis-(4-fluorophenyl)ethene. Elution through silica gel, with toluene, removes the latter to leave a colorless liquid which is pure 1,1-bis(4-fluorophenyl)ethanol (b.p. 103°/0.09 mm Hg; with slight decomposition).

P.m.r. spectrum: (CDCl$_3$/TMS): 1.90 (3H: singlet); 2.11 (1H: labile singlet); 6.80–7.60 (8H: aromatic complex).

4,4'-Difluorobenzophenone may be obtained, for example, as described in J.prakt.Chem., 135, 245–266 (1932) or in European Patent Publication No. 4710.

EXAMPLE 2

To a mixture of 1,1-bis(4-fluorophenyl)ethene (28.5 parts) in water (1500 parts) (acidified to pH 1.0 with conc. hydrochloric acid) at reflux, is added sodium hypochlorite solution (400 parts) (2.6% w/v Cl$_2$) over 5 hours. The mixture is thoroughly extracted with carbon tetrachloride (200 parts) which is then washed with water (200 parts) and dried over anhydrous sodium sulphate. Removal of the solvent under vacuum leaves a brown, low melting point solid (36.5 parts) which contains 75.7% 1,1-bis(4-fluorophenyl)-2-chloroethanol (by quantitative PMR) (78% conversion based on 1,1-bis(4-fluorophenyl)ethene). Recrystallisation twice from petroleum ether (100°–200° ) and once from hexane gives fine white needles (19.9 parts) of pure 1,1-bis(4-fluorophenyl)-2-chloroethanol (56.3% yield based on 1,1-bis(4-fluorophenyl)ethene (m.pt. 83°–84° C.). (Found: 62.3% C; 4.3% H; 13.4% Cl; 14.3% F. C$_{14}$H$_{11}$ClF$_2$O requires: 62.6% C; 4.1% H; 13.2% Cl; 14.1% F).

P.m.r. spectrum: (CCl$_4$/TMS): 2.99 (1H: labile singlet); 4.01 (2H: singlet); 6.80–7.50 (8H: aromatic complex).

The 1,1-bis(4-fluorophenyl)ethene used in this Example may be prepared as described in J. Chem. Soc., 567–570 (1942).

EXAMPLE 3

To a mixture of 1,1-bis(4-fluorophenyl)ethene (28.5 parts) in water (1500 parts), at reflux, is added a solution of potassium bromide (36 parts) and bromine (28.8 parts) in water (295 parts), over 3 hours. The mixture is thoroughly extracted with carbon tetrachloride (200 parts) which is then washed with water (200 parts) and dried over anhydrous sodium sulphate. Removal of solvent under vacuum leaves a brown, low melting point solid (41.3 parts) which contains 69.3% (by PMR) 1,1-bis(4-fluorophenyl)-2-bromoethanol (70.4% conversion based on 1,1-bis-(4-fluorophenyl)ethene. Recrystallisation from petroleum ether (100°–200°) gives fine white needles (20.4 parts) of pure 1,1-bis(4-fluorophenyl)-2-bromoethanol (49.3% yield based on 1,1-bis(4-fluorophenyl)ethene (m.pt. 72.5°–73.5° C.).

(Found: 53.6% C; 3.5% H; 12.1% F; 25.2% Br. C$_{14}$H$_{11}$BrF$_2$O requires: 53.7% C; 3.5% H; 12.1% F; 25.5% Br).

P.m.r. spectrum: (CDCl$_3$/TMS): 3.08 (1H: labile singlet); 4.03 (2H: singlet); 6.85–7.50 (8H: aromatic complex).

EXAMPLE 4

1-(2-Fluorophenyl)-1-(4-fluorophenyl)-2-bromoethanol 1-(2-Fluorophenyl)-1-(4-fluorophenyl) ethene (64.8 parts) was added slowly to a solution of sulphuric acid (27.5 parts) in water (500 parts) at 80° C.; at the same time was added 114 parts by volume of a solution containing sodium bromide (22 parts) and sodium bromate (16 parts). Addition was complete after 1 hour 40 minutes. After stirring at 80° for a further 30 minutes, the mixture was stirred overnight, allowing the temperature to fall back to 20°–25° C. A P.M.R. spectrum of the organic layer showed no residual alkene. The mixture was extracted once with chloroform (75 parts) and the lower layer separated off. Removal of the chloroform under vacuum gave a brown liquid (103.6 parts) containing 57.3 parts of 1-(2-fluorophenyl)1-(4-fluorophenyl)-2-bromoethanol (61% of theoretical yield; analysis by H.P.L.C.).

We claim:

1. A process for the preparation of the halohydrins of formula (I):

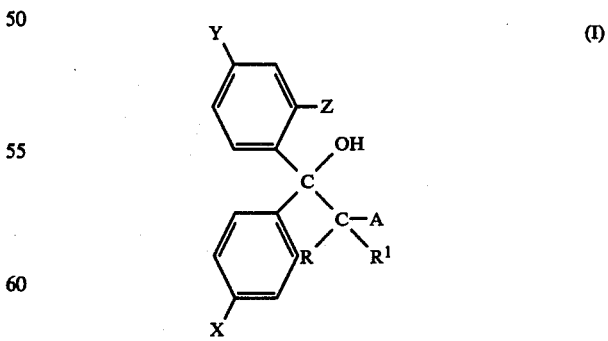

wherein R and R$^1$, which may be the same or different, are hydrogen or alkyl; X, Y and Z are each independently hydrogen, chlorine or fluorine and A is chlorine or bromine, which comprises reacting a tertiary alcohol of general formula (II):

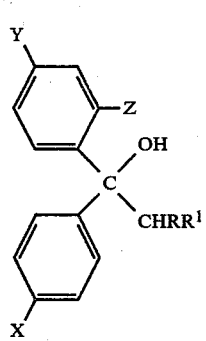
or a substituted alkene of general formula (III):
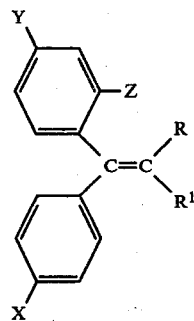
with chlorine, bromine, hypochlorous acid or hypobromous acid in water at a pH not exceeding 7 and at a temperature from 10° to 150° C.
2. A process as set forth in claim 1 in which the starting material is said tertiary alcohol.
* * * * *